United States Patent
Chan (10) Patent No.: US 12,076,474 B2
(45) Date of Patent: Sep. 3, 2024

(54) METHOD OF TREATING TRAUMATIC BRAIN INJURY

(71) Applicant: CYTOSORBENTS CORPORATION, Monmouth Junction, NJ (US)

(72) Inventor: Phillip Chan, Cherry Hill, NJ (US)

(73) Assignee: CytoSorbents, Inc., Princeton, NJ (US)

( * ) Notice: Subject to any disclaimer, the term of this patent is extended or adjusted under 35 U.S.C. 154(b) by 999 days.

(21) Appl. No.: 16/614,838

(22) PCT Filed: May 21, 2018

(86) PCT No.: PCT/US2018/033661
§ 371 (c)(1),
(2) Date: Nov. 19, 2019

(87) PCT Pub. No.: WO2018/217629
PCT Pub. Date: Nov. 29, 2018

(65) Prior Publication Data
US 2020/0086032 A1 Mar. 19, 2020

Related U.S. Application Data (60) Provisional application No. 62/509,790, filed on May 23, 2017.

(51) Int. Cl.
| | | |
|---|---|---|
| *B01D 15/00* | (2006.01) | |
| *A61K 31/717* | (2006.01) | |
| *A61M 1/36* | (2006.01) | |
| *A61M 31/00* | (2006.01) | |
| *B01J 20/24* | (2006.01) | |
| *B01J 20/26* | (2006.01) | |
| *B01J 20/28* | (2006.01) | |
| *B01J 20/30* | (2006.01) | |
| *B01J 20/32* | (2006.01) | |

(52) U.S. Cl.
CPC .......... *A61M 1/362* (2014.02); *A61K 31/717* (2013.01); *A61M 1/3679* (2013.01); *A61M 1/3687* (2013.01); *A61M 31/00* (2013.01); *B01J 20/24* (2013.01); *B01J 20/264* (2013.01); *B01J 20/267* (2013.01); *B01J 20/28004* (2013.01); *B01J 20/28016* (2013.01); *B01J 20/28069* (2013.01); *B01J 20/28073* (2013.01); *B01J 20/28076* (2013.01); *B01J 20/28083* (2013.01); *B01J 20/28085* (2013.01); *B01J 20/28092* (2013.01); *B01J 20/3078* (2013.01); *B01J 20/3282* (2013.01)

(58) Field of Classification Search
CPC .. A61M 1/362; A61M 1/3679; A61M 1/3687; A61M 31/00; A61M 1/3655; A61M 1/3692; A61M 1/36; A61M 1/3601; A61M 1/3621; A61M 1/3633; A61M 1/3635; A61K 31/717; B01J 20/24; B01J 20/264; B01J 20/267; B01J 20/28004; B01J 20/28016; B01J 20/28069; B01J 20/28073; B01J 20/28076; B01J 20/28083; B01J 20/28085; B01J 20/28092; B01J 20/3078; B01J 20/3282; B01J 2220/62; B01J 20/3208; B01J 20/3276; B01D 15/00
USPC ......................................................... 422/44
See application file for complete search history.

(56) References Cited

U.S. PATENT DOCUMENTS

| | | | |
|---|---|---|---|
| 4,265,768 A | 5/1981 | Beasley et al. | |
| 7,556,768 B2* | 7/2009 | Brady ................ | A61P 29/00 422/44 |
| 8,535,258 B2* | 9/2013 | Matson ............... | A61M 1/3472 604/6.09 |
| 2003/0100857 A1 | 5/2003 | Pedrazzi et al. | |
| 2011/0124721 A1 | 5/2011 | Wang et al. | |
| 2012/0238441 A1 | 9/2012 | Young et al. | |
| 2013/0011824 A1* | 1/2013 | Chan ................... | B01J 20/328 210/691 |
| 2013/0195792 A1* | 8/2013 | Chan ................... | A61P 9/10 424/78.31 |
| 2015/0118673 A1* | 4/2015 | Chan ................... | B01J 20/28016 502/402 |
| 2015/0335576 A1* | 11/2015 | Chan ................... | A61P 39/02 210/287 |

FOREIGN PATENT DOCUMENTS

| | | |
|---|---|---|
| AU | 2012204271 B2 | 8/2015 |
| CN | 103037869 A | 4/2013 |
| EP | 3173145 A1 | 5/2017 |
| JP | 2013-523772 A | 6/2013 |
| JP | 2015-530969 A | 10/2015 |
| WO | WO 2011/123767 A1 | 10/2011 |
| WO | WO 2016/013540 A1 | 1/2016 |
| WO | 2017070415 A1 | 4/2017 |

OTHER PUBLICATIONS

International Patent Application No. PCT/US2018/033661; Int'l Search Report and the Written Opinion; dated Aug. 3, 2018; 19 pages.
International Patent Application No. PCT/US2018/033661; Int'l Preliminary Report on Patentability; dated Nov. 20, 2019; 12 pages.
European Patent Application No. 18806164.2; Extended Search Report; dated Jan. 18, 2021; 8 pages.
McKinley, Todd O., et al. "Blood purification by nonselective hemoadsorption prevents death after traumatic brain injury and hemorrhagic shock in rats." *Journal of Trauma and Acute Care Surgery* 85.6 (2018): 1063-1071.

* cited by examiner

*Primary Examiner* — Frank M Lawrence, Jr.
(74) *Attorney, Agent, or Firm* — BakerHostetler (57) ABSTRACT

The present invention concerns methods of treating a patient suffering from a traumatic brain injury (TBI), comprising contacting said patient's blood with a sorbent for an inflammatory mediator and kits for performing such treatments.

15 Claims, 10 Drawing Sheets

METHOD OF TREATING TRAUMATIC BRAIN INJURY

CROSS-REFERENCE TO RELATED APPLICATIONS

The invention is the National Stage Application of International Patent Application No. PCT/US2018/033661 filed May 21, 2018 which claims benefit of U.S. Patent Application No. 62/509,790, filed on May 23, 2017, which is incorporated herein in its entirety.

TECHNICAL FIELD

The invention concerns, inter alia., methods of treating traumatic brain injury.

BACKGROUND

An inflammatory response occurs quickly following a traumatic brain injury (TBI). The response is characterized by the release of certain cytokines having pro- and anti-inflammatory functions. There is a need in the art for treatments that improve survival of victims of such injuries.

SUMMARY

In some aspects, the invention concerns methods of treating a patient suffering from a traumatic brain injury (TBI), comprising contacting said patient's blood with a sorbent for one or more inflammatory mediators resulting from such injury. In certain embodiments, the sorbent comprises any of the polymers described herein.

In other aspects, the invention relates to kits comprising a cartridge comprising a sorbent for inflammatory mediators related to traumatic brain trauma. The kits may contain any of the polymers described herein. In some embodiments, the kit comprises instructions for use of the cartridge. Some instructions are contained on a label attached to the cartridge.

DETAILED DESCRIPTION OF ILLUSTRATIVE EMBODIMENTS

An inflammatory response occurs quickly following a traumatic brain injury (TBI). The response is characterized by the release of toxins such as certain cytokines having pro- and anti-inflammatory functions. The instant disclosure is directed to treatment of such injury by removing certain toxins from a patient's blood.

In some aspects, the invention concerns methods of treating a patient suffering from a traumatic brain injury (TBI), comprising contacting said patient's blood with a sorbent for one or more inflammatory mediators resulting from such injury. In certain embodiments, the sorbent comprises any of the polymers described herein.

Some treatment methods involve a circuit for removing blood from said patient, contacting the blood with the sorbent and returning said blood to the patient. In certain embodiments, the sorbent is in a cartridge and blood is taken from an appropriate artery and returned to the patient through an appropriate vein.

In other aspects, the invention relates to kits comprising a cartridge comprising a sorbent for inflammatory mediators related to traumatic brain trauma. The kits may contain any of the polymers described herein. In some embodiments, the kit comprises instructions for use of the cartridge. Some instructions are contained on a label attached to the cartridge. Some kits additionally comprising means for removing blood from said patient, contacting the blood with the sorbent and returning said blood to the patient.

In some embodiments, the polymer materials used as the sorbent are substantially not metabolizable by human and animal. Certain polymers may be irregular or regular shaped particulates such as powders, beads, or other forms with a diameter in the range of 0.1 micron meters to 2 centimeters The polymers used in the instant invention preferably have a biocompatible and hemocompatible exterior surface coatings but are not absolutely necessary, especially in certain circumstances, such as oral or rectal administration. Certain of these coatings are covalently bound to the polymer particle (beads, for example) by free-radical grafting. The free-radical grafting may occur, for example, during the transformation of the monomer droplets into polymer beads. The dispersant coating and stabilizing the monomer droplets becomes covalently bound to the droplet surface as the monomers within the droplets polymerize and are converted into polymer. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

By "biocompatible", it is meant that the polymer is capable of contact with living tissues or organisms without causing harm during the time that the polymer is in contact with the tissue or organism. In some embodiments, it is intended that the polymer is tolerated by the gut and alimentary canal of the organism. The polymers of the present invention are preferably non-toxic.

In some embodiments, the polymer has a preferential pore structure such that the total pore volume of pore size in the range of 50 Å to 3000 Å is greater than 0.5 cc/g to 3.0 cc/g dry polymer; wherein the ratio of pore volume between 50 Å to 3,000 Å (pore diameter) to the pore volume between 500 Å to 3,000 Å (pore diameter) of the polymer is smaller than 200:1; and the ratio of pore volume between 50 Å to 3,000 Å in diameter to the pore volume between 1,000 Å to 3,000 Å in diameter of the polymer is greater than 20:1. The said ratios can be alternatively specified in terms of pore surface area (such as the ratio of pore surface area between 50 Å to 3,000 Å to pore surface area between 500 Å to 3,000 Å of the polymer); and therefore is an alternative way of specifying the same pore structure.

Some preferred polymers are coated polymers comprising at least one crosslinking agent and at least one dispersing agent. Suitable dispersing agents include hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof.

Suitable crosslinking agents include divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the polymer is developed simultaneously with the formation of the coating, such that the dispersing agent gets chemically bound to the surface of the polymer.

Preferred polymers include those derived from one or more monomers selected from divnylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

Some preferred polymers are ion exchange polymers.

Some preferred polymers are cellulosic polymers. Suitable polymers include cross-linked dextran gels such as Sephadex®.

Certain preferred polymers are porous highly crosslinked styrene or divinylbenzene copolymer. Some of these polymers are a macroporous or mesoporous styrene-divinylbenzene-ethylstyrene copolymer subjected to a partial chloromethylation to a chlorine content of up to 7% molecular weight. Other of these polymers are a hypercrosslinked polystyrene produced from crosslinked styrene copolymers by an extensive chloromethylation and a subsequent post-crosslinking by treating with a Friedel-Crafts catalyst in a swollen state. Yet other of these polymers are a hypercrosslinked polystyrene produced from crosslinked styrene copolymers by an extensive additional post-crosslinking in a swollen state with bifunctional crosslinking agents selected from the group comprising of monochlorodimethyl ether and p-xylilene dichloride Some polymers useful in the practice of the invention are hydrophilic self-wetting polymers that can be administered as dry powder containing hydrophilic functional groups such as, amines, hydroxyl, sulfonate, and carboxyl groups.

Certain polymers useful in the invention are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex® Optipore™ L-493, Dowex® Optipore™ V-493, Dowex® Optipore™ V-502, Dowex® Optipore™ L-285, Dowex® Optipore™ L-323, and Dowex® Optipore™ V-503. Lanxess (formerly Bayer and Sybron): Lewatit® VPOC 1064 MD PH, Lewatit® VPOC 1163, Lewatit® OC EP 63, Lewatit® S 6328A, Lewatit® OC 1066, and Lewatit® 60/150 MIBK. Mitsubishi Chemical Corporation: Diaion® HP 10, Diaion® HP 20, Diaion® HP 21, Diaion® HP 30, Diaion® HP 40, Diaion® HP 50, Diaion® SP70, Diaion® SP 205, Diaion® SP 206, Diaion® SP 207, Diaion® SP 700, Diaion® SP 800, Diaion® SP 825, Diaion® SP 850, Diaion® SP 875, Diaion® HP 1MG, Diaion® HP 2MG, Diaion® CHP 55A, Diaion® CHP 55Y, Diaion® CHP 20A, Diaion® CHP 20Y, Diaion® CHP 2MGY, Diaion® CHP 20P, Diaion® HP 20SS, Diaion® SP 20SS, and Diaion® SP 207SS. Purolite Company: Purosorb™ AP 250 and Purosorb™ AP 400.

Traumatic brain injury can produce damage-associated molecular pattern (DAMPs) molecules that include (1) molecules that perform noninflammatory functions in living cells (such as HMGB1) and acquire immunomodulatory properties when released, secreted, modified, or exposed on the cell surface during cellular stress, damage, or injury, or (2) alarmins, i.e., molecules that possess cytokine-like functions (such as β-Defensins and Cathelicidin), which can be stored in cells and released upon cell lysis, whereupon they contribute to the inflammatory response. When released outside the cell or exposed on the surface of the cell following tissue injury, they move from a reducing to an oxidizing milieu, which affects their activity. Also, following necrosis, mitochondrial and nuclear DNA fragments are released outside the cell becoming DAMPs. Certain cytokines having pro- and anti-inflammatory functions are important toxins produced by traumatic brain injury.

The invention also relates to kits comprising a cartridge comprising a sorbent for inflammatory mediators related to traumatic brain trauma. The kits may contain any of the polymers described herein. In some embodiments, the kit comprises instructions for use of the cartridge. Some instructions are contained on a label attached to the cartridge.

As used herein, the term "sorbent" includes adsorbents and absorbents.

As used herein, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The sorbents are typically are contained within a cartridge adapted to allow blood to flow into the cartridge and then exit the cartridge and then be returned to the patient's body. Although cartridges are typically utilized, other containers that allow blood to contact the sorbent and then be returned to the patient may also be utilized.

In some embodiments, blood is taken from an appropriate artery and returned to within the patient through an appropriate vein. Methods of establishing a circuit to remove and return blood to the patient's body are well known by those skilled in the art.

Sorbent for use outside of the body may be provided in pre-loaded cartridges. Such cartridges may have one or more screens to prevent the sorbent from leaving the cartridge during use.

Alternately, in some embodiments, the sorbent may be administered within an animal's body. In some preferred embodiments, the animal is human. In certain embodiments, the dose of sorbent is administered orally, via a feeding tube, peritoneally, or rectally.

Some polymers can be supplied as a slurry, or suspension, or dry powder or other dry particulate capable of being wetted. In some methods, the sorbent is supplied as a slurry or suspension packaged in either single dose or multidose packages for oral administration. In other methods, the sorbent is supplied as a slurry or suspension packaged in either single dose or multidose packages for administration by enema or feeding tube or any combination therein.

The polymer can also be supplied as a dry powder or other dry particulate capable of being wetted externally or internally in the alimentary canal, including in the gastric or enteric environment, with or without the addition of wetting agents such as ethyl or isopropyl alcohol. In yet other embodiments, the polymer is supplied as tablet, dry powder, other dry particulate, capsule or suppository packaged in bottles or blister packs for administration.

In some methods, the polymer materials are not metabolizable by human and animal.

The compositions of the instant invention may be administered by methods well known to those skilled in the art. In some embodiments, administration is topical. Such methods include ophthalmic administration, administration to skin or wounds, direct administration into a body cavity or joint, and delivery to mucous membranes such as nasal, oral, vaginal and rectal delivery or other delivery to the alimentary canal. In some embodiments, such methods include local or systemic administration through an oral or parenteral route. In some embodiments, the treatment is extracorporeal. Extracorporeal administration would include removal of inflammatory mediators from blood or physiologic fluids by circulating the fluids through a device containing sorbent and returning it back to the body. Parenteral administration includes intravenous, intraarterial, subcutaneous, intraperitoneal or intramuscular injection or infusion; or intracranial (including intrathecal or intraventricular, administration).

Pharmaceutical compositions and formulations for topical administration include but are not limited to ointments, lotions, creams, transdermal patches, gels, drops, suppositories, sprays, liquids and powders. Utilization of conventional pharmaceutical carriers, oily bases, aqueous, powder, thickeners and the like may be used in the formulations.

The pharmaceutical compositions may also be administered in tablets, capsules, gel capsules, slurries, suspensions, and the like.

Penetration enhancers may also be used in the instant pharmaceutical compositions. Such enhancers include surfactants, fatty acids, bile salts, chelating agents, and non-chelating non-surfactants and are generally known in the art.

The polymers of the present invention can be administered once to a patient or in multiple doses. Determination of the amounts of administration are within the skill level of one skilled in the art.

Polymers useful in the invention may be supplied as a slurry, suspension or reconstituted from the dry state into a slurry or suspension. In some embodiments, the polymer may be supplied as a slurry or suspension packaged in either single dose or multidose bottles for oral administration. In other embodiments, the polymer may be supplied as a slurry or suspension packaged in either single dose or multidose bottles for administration by enema or feeding tube or any combination therein. In certain embodiments, the polymer is supplied as a dry powder capable of being wetted externally or in the alimentary canal with or without the addition of wetting agents such as ethyl alcohol.

The polymer may be supplied as tablet, capsule or suppository packaged in bottles or blister packs for administration. Depending on the use, the polymer may be sterile or non-sterile. The polymer may be sterilized by standard methods. Such methods are well known to those skilled in the art.

The following examples are intended to be illustrative and not limiting.

EXPERIMENTAL

Traumatic brain injury (TBI) was induced using the closed cortical impact (CCI) model (IACUC Approved Protocol). Rats were anesthetized via a nasal mask, and the rat's head was secured to a stereotaxic frame (David Kopf Instruments). A 7-mm craniotomy was made between the lambda and bregma and centered over the right fronto-parietal cortex lateral to the central suture with dura intact. The impact device (Benchmark Stereotaxic Impactor; Myneurolab) struck the right fronto-parietal cortex with a velocity of 4 m/s, tissue deformation of 2.5 mm, and impact duration of 100 ms with a 5-mm impactor tip. Rats were afforded standard post-injury analgesics.

Subsequently, the rats were subjected to Hemorrhagic Shock (HS) through a controlled bleed from the femoral artery at 0.5 ml/min to a Systolic Blood Pressure (SBP) of 40 which was maintained for 60 minutes. Rats were resuscitated with shed blood and saline. At the conclusion of the injury, rats were treated with Cytosorbents' Cytosorb™ porous polymer bead technology using a 2 ml cartridge in series with the femoral artery and femoral vein. Rats were treated for three hours and then transferred back to their cages for free activity and food.

Figure 1:
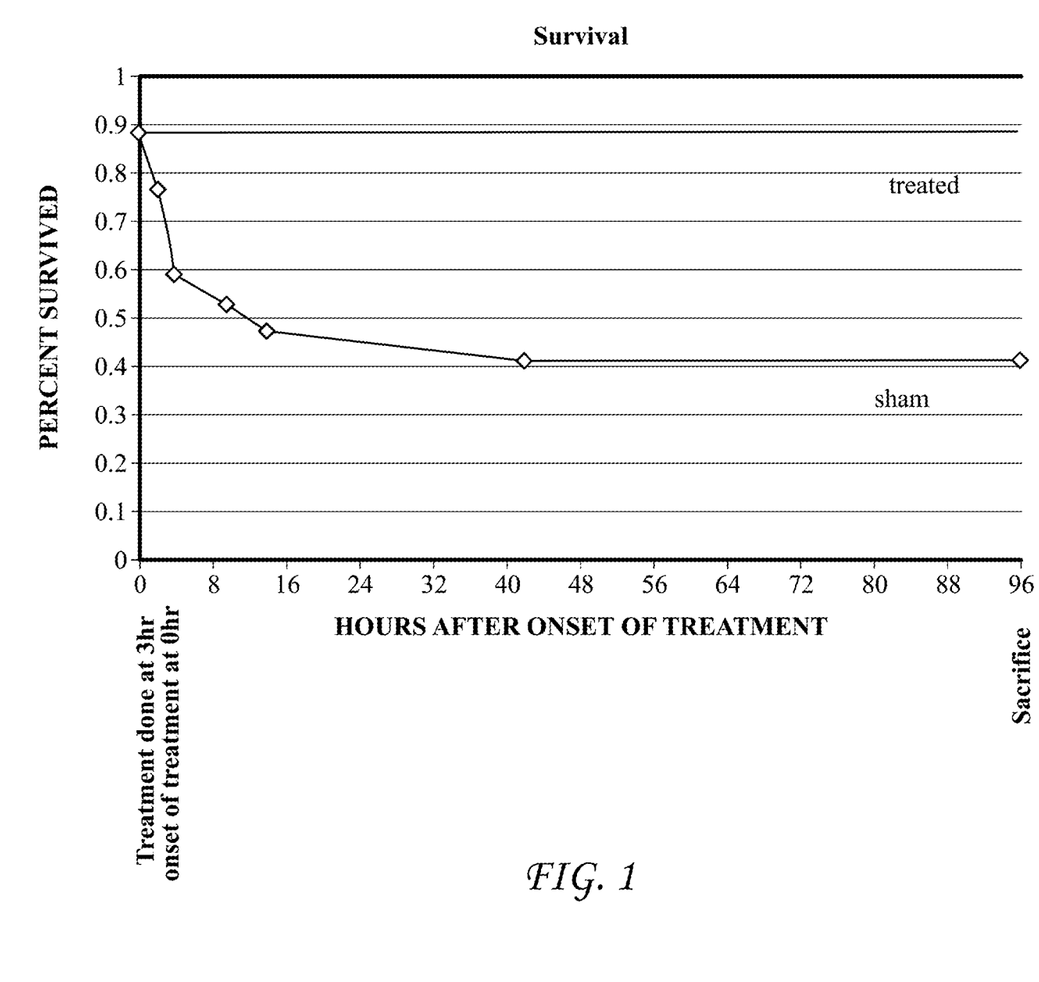
FIG. 1 shows survival rates of rats having actual treatment versus sham treatment.

Survival rates of rats who received sorbent treatment and those who were treated with a placebo (sham treatment) were compared. Two rats from the Sham and Treatment groups did not survive the injury and died before treatment. As such, the survival curve starts around 88%. Eighteen rats were treated and 17 got sham treatment. The survival curve and changes in 27 trauma-related cytokines are shown in FIG. 1.

Figure 2:
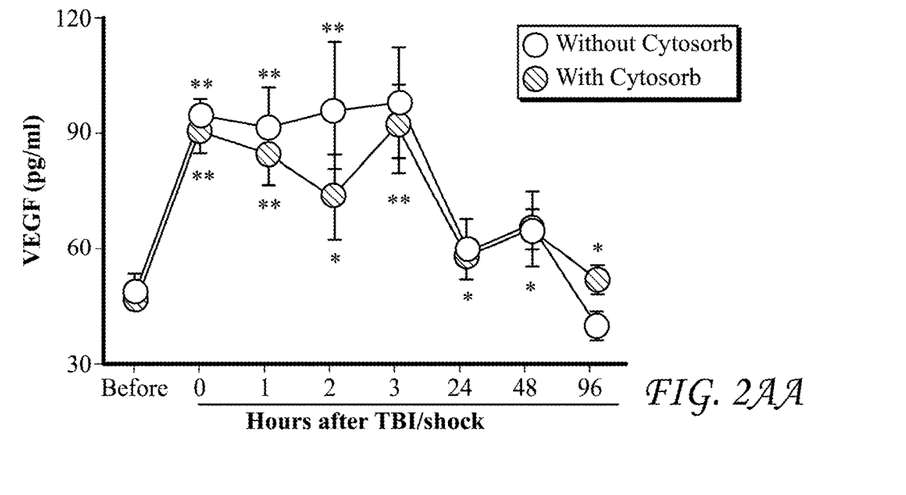
Figure 2A:
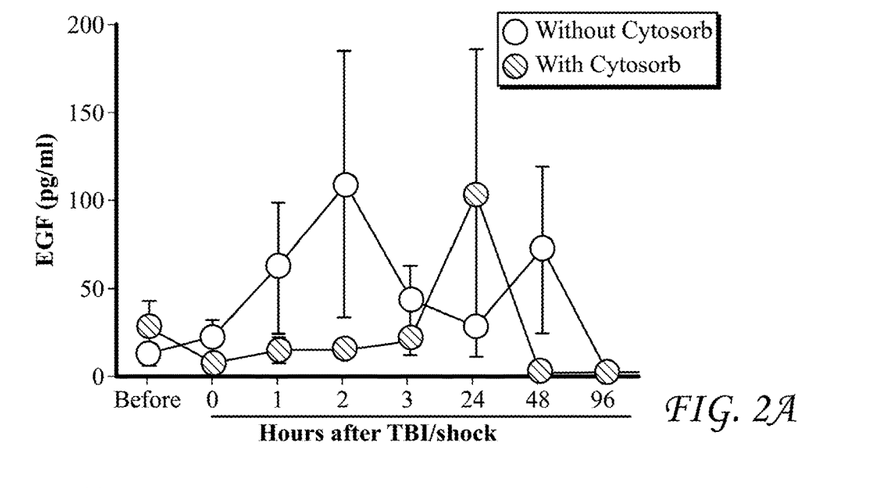
FIGS. 2A-2AA show levels of certain inflammatory mediators after traumatic brain injury over time with an actual treatment and a sham treatment.
Figure 2B:
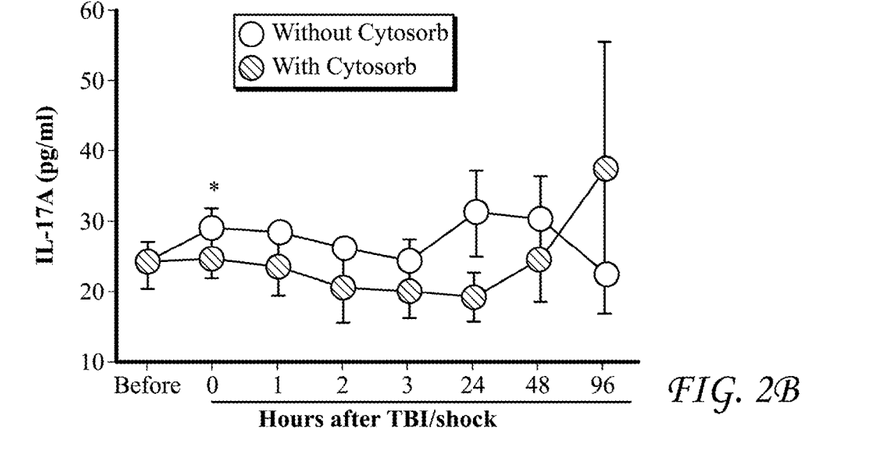
Figure 2C:
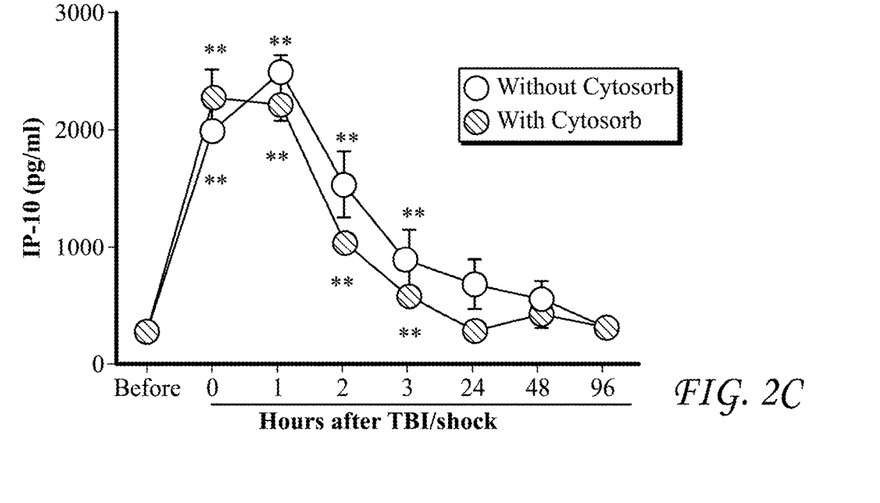
Figure 2D:
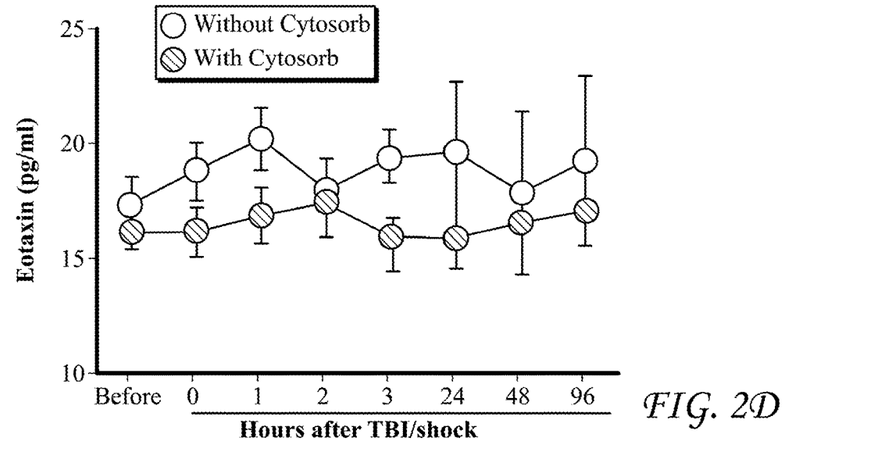
Figure 2E:
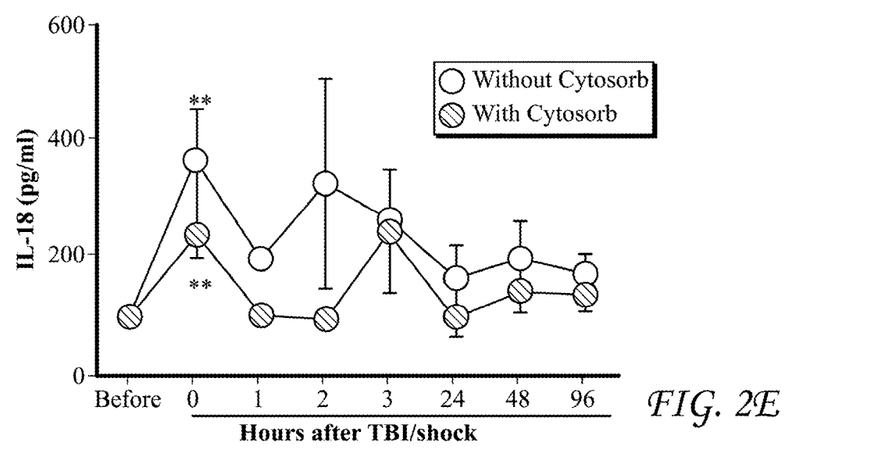
Figure 2F:
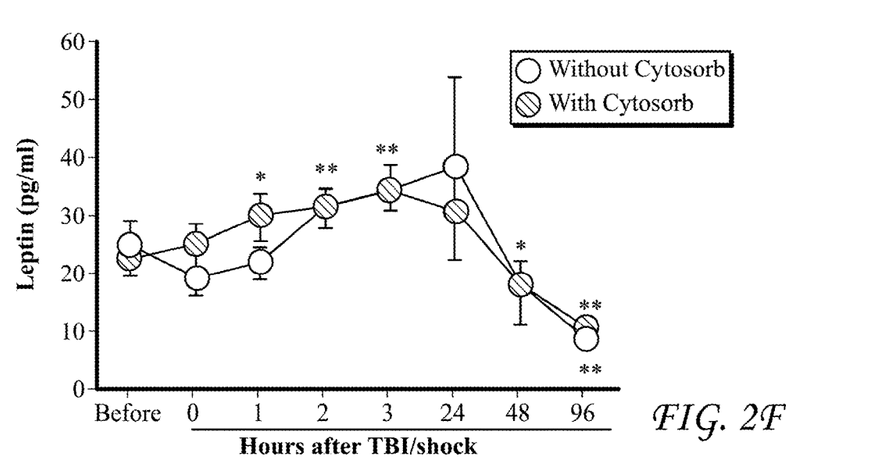
Figure 2G:
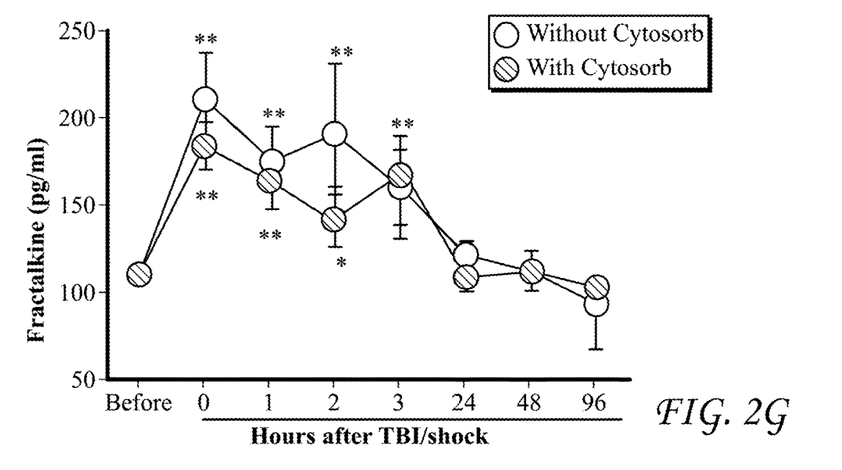
Figure 2H:
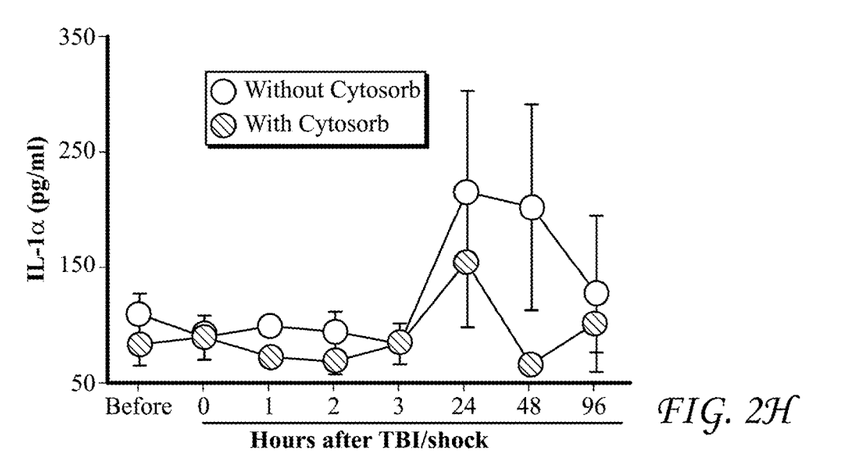
Figure 2I:
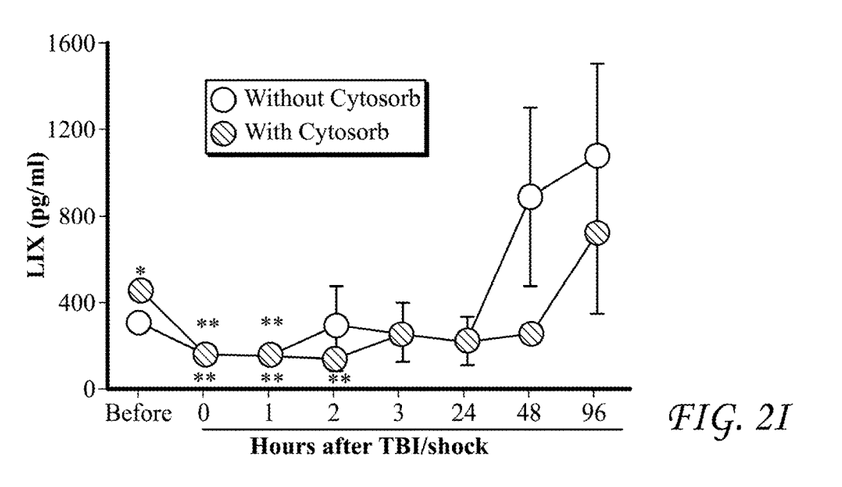
Figure 2J:
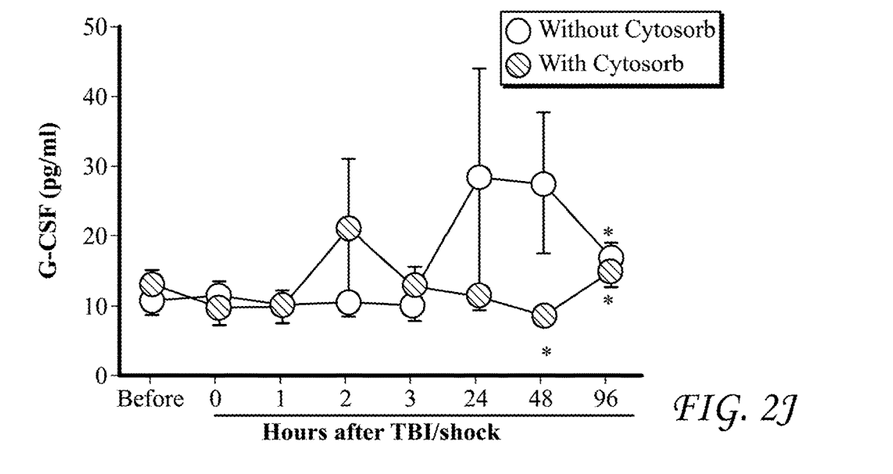
Figure 2K:
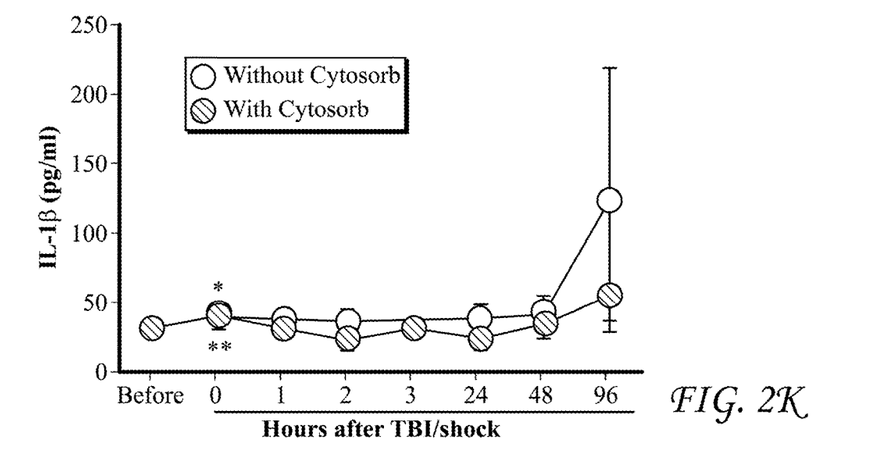
Figure 2L:
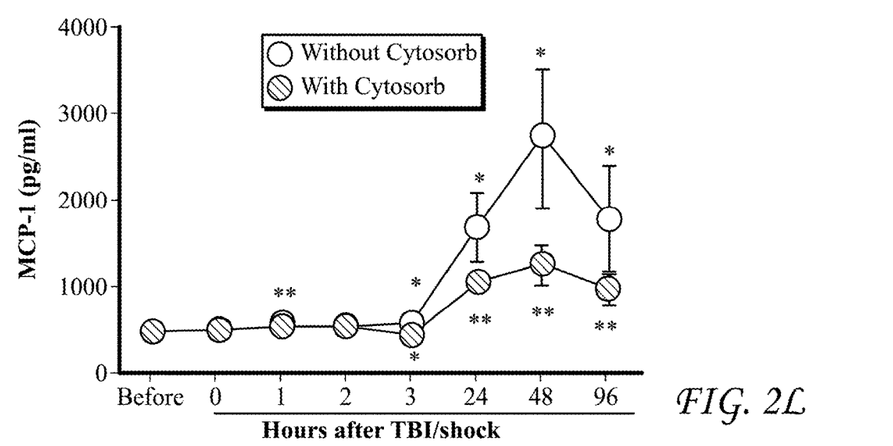
Figure 2M:
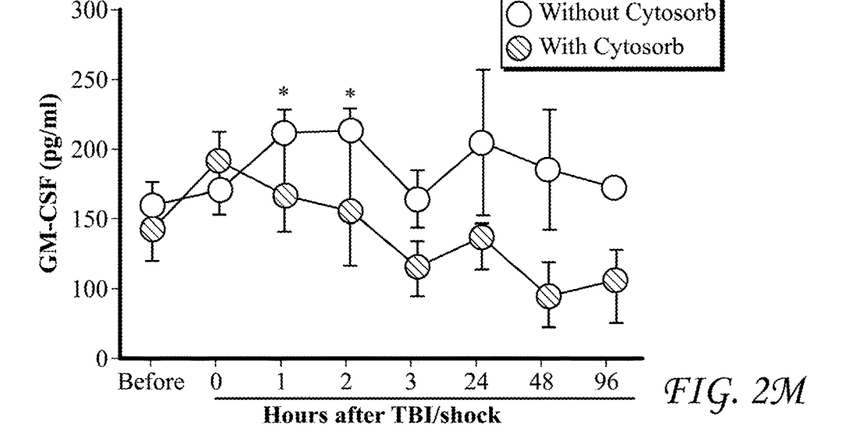
Figure 2N:
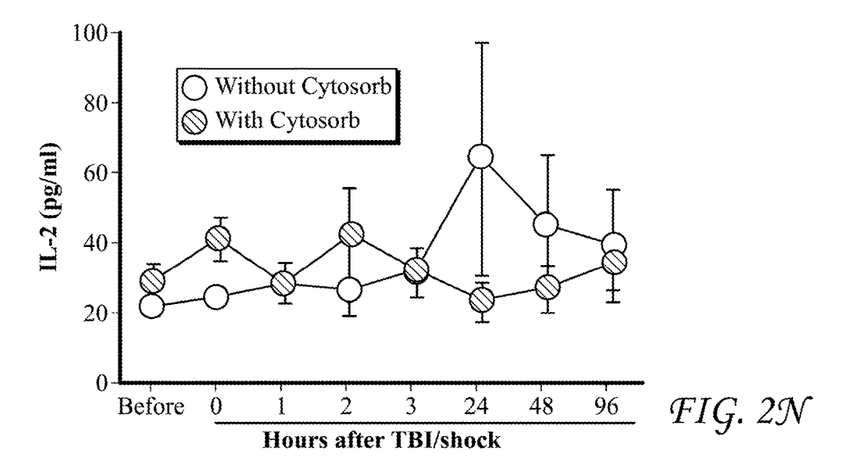
Figure 2O:
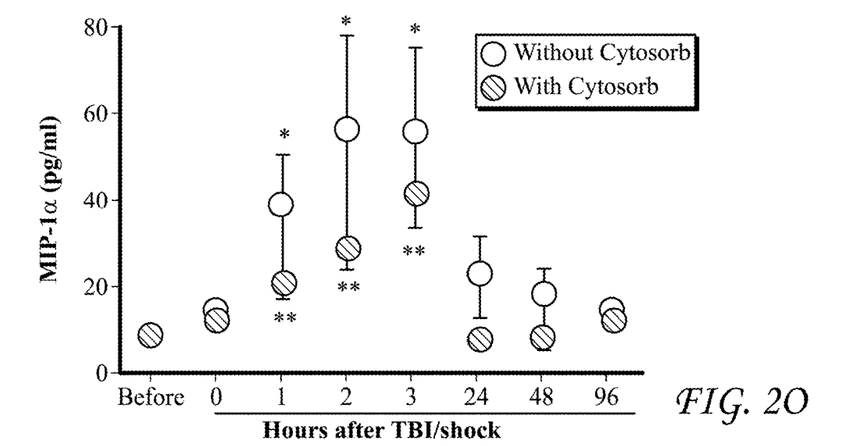
Figure 2P:
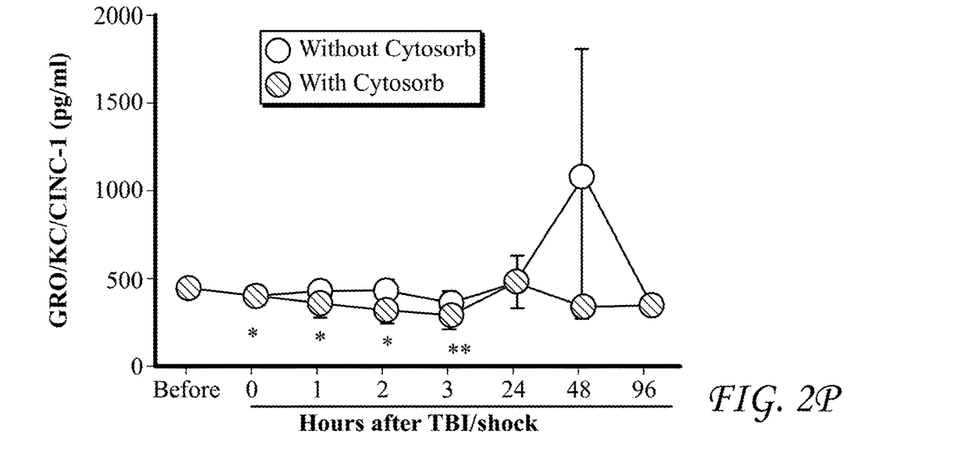
Figure 2Q:
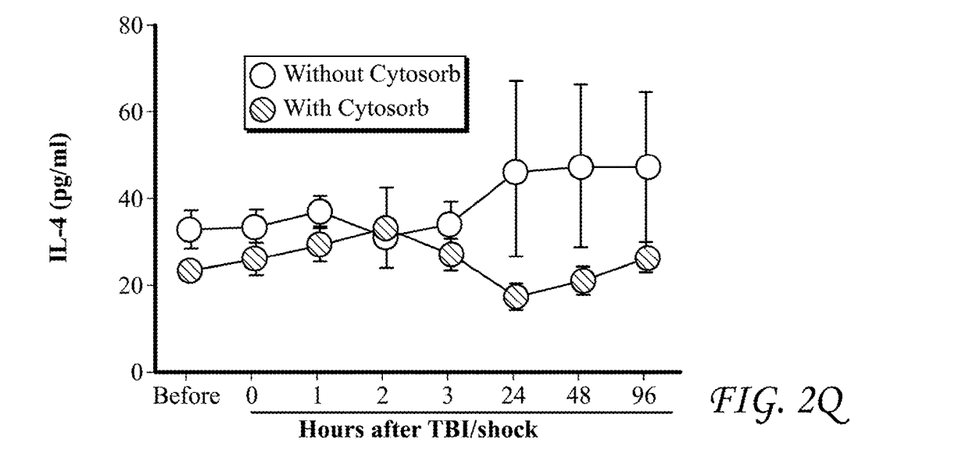
Figure 2R:
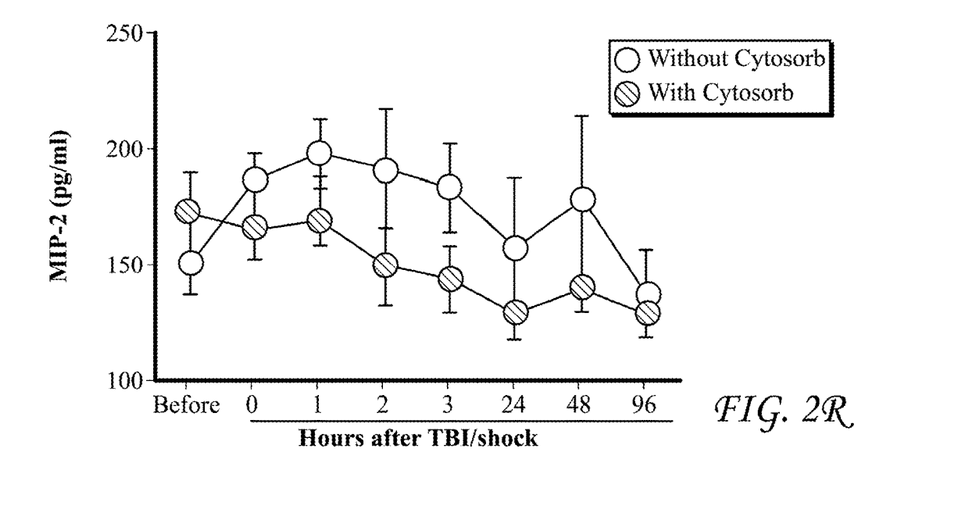
Figure 2S:
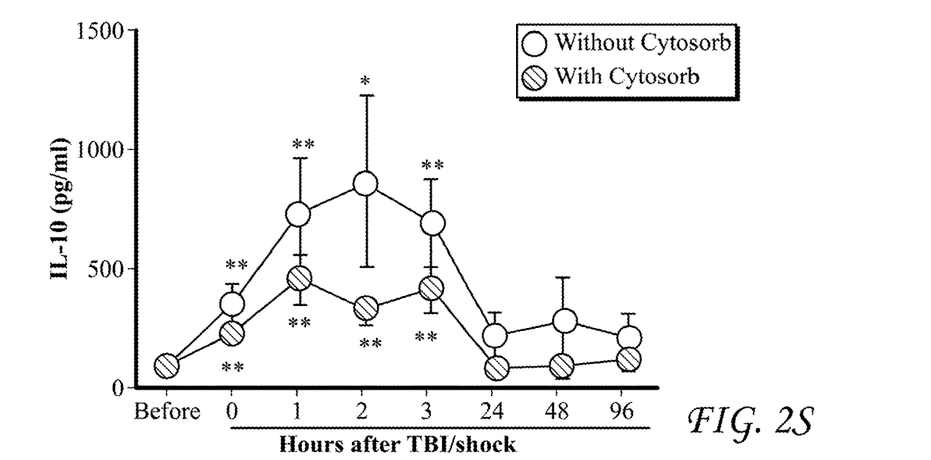
Figure 2T:
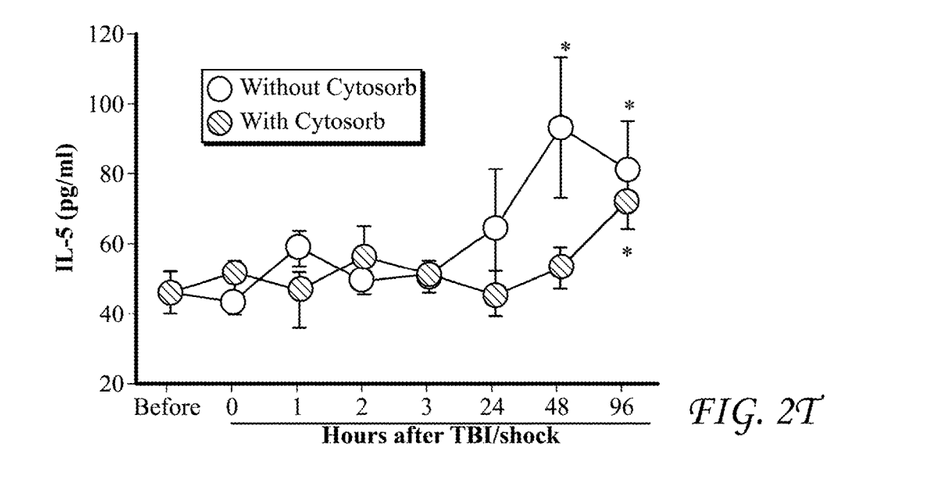
Figure 2U:
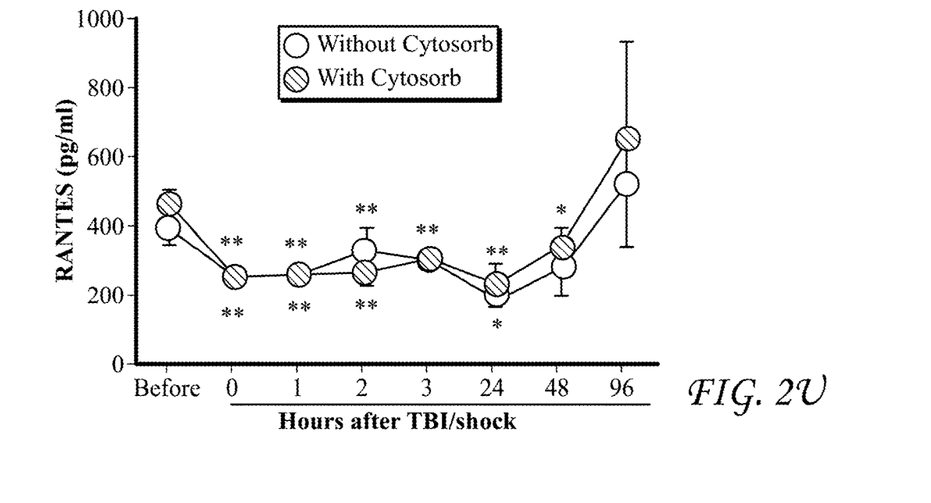
Figure 2V:
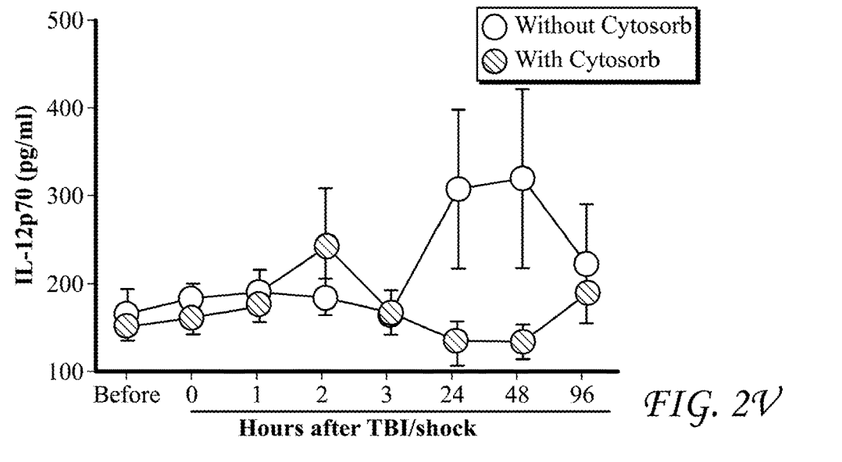
Figure 2W:
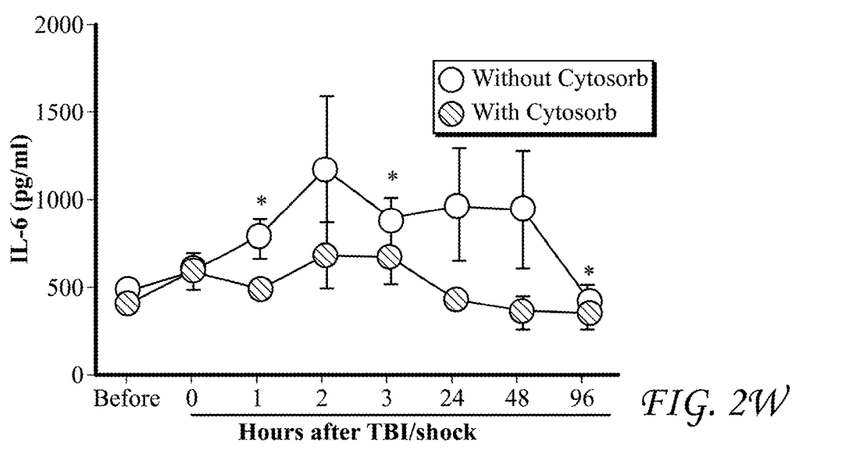
Figure 2X:
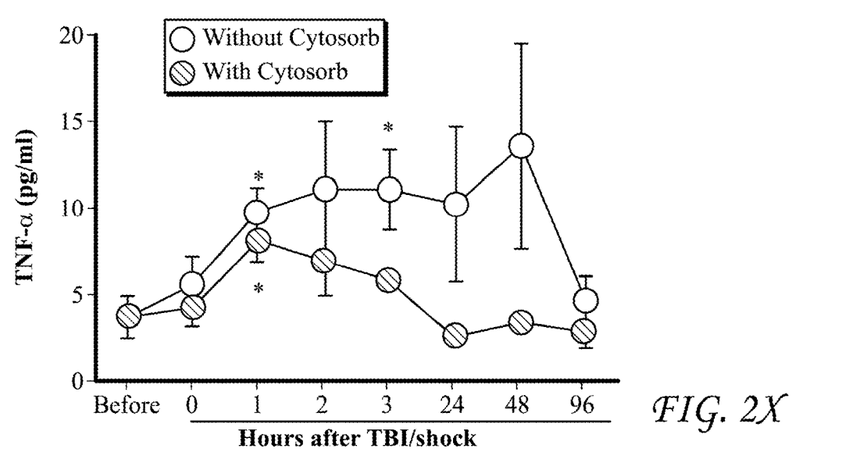
Figure 2Y:
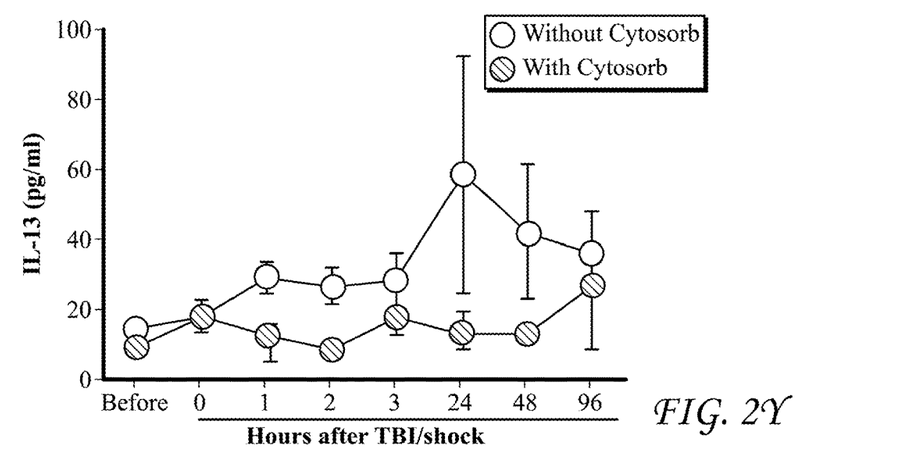
Figure 2Z:
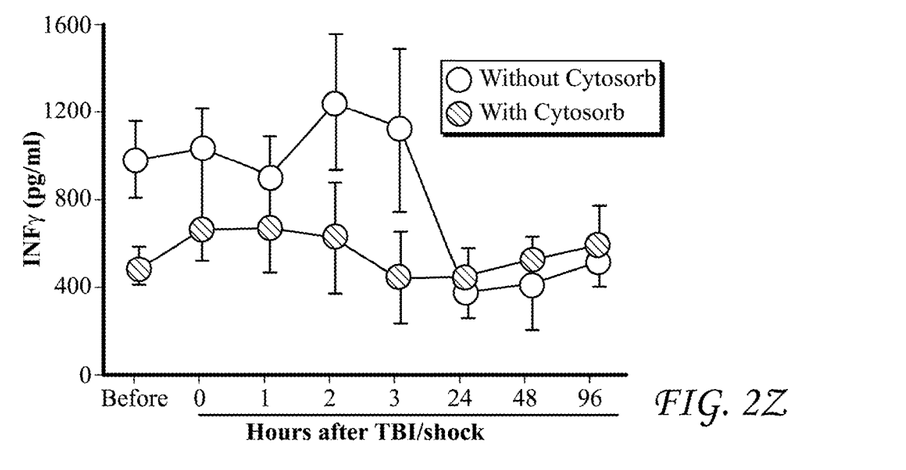

FIG. 2 shows lower levels of several inflammatory mediators in rats treated with sorbent and placebo. Inflammatory mediators include EGF (epidermal growth factor), interleukin factors (such as IL-1α, IL-1β, IL-2, IL-4, IL-5, IL-6, IL-10, Il-12, IL-13, IL-17, IL-18), monocyte chemoattractant protein 1 (MCP-1), granulocyte colony-stimulating factor (G-CSF), granulocyte-macrophage colony-stimulating factor (GM-CSF), eotaxin, macrophage Inflammatory Proteins (such as MIP-1 and MIP-2), tumor-necrosis factor-alpha (TNF-alpha), vascular endothelial cell growth factor (VEGF), gamma interferon (IFN-γ), rantes, and keratinocyte chemoattractant (KC)/human growth-regulated oncogene (GRO) chemokines.

In further examples, sorbents are administered orally, via a feeding tube, peritoneally, or rectally to reduce inflammatory mediators related to TBI.

What is claimed:

1. A method of treating a patient suffering from a traumatic brain injury (TBI), comprising contacting said patient's blood with a sorbent for an inflammatory mediator; wherein said sorbent comprises a biocompatible polymer; wherein:
said biocompatible polymer has a pore structure that the total pore volume of pore size in the range of 50 Å to 3000 Å is from about 0.5 cc/g to 3.0 cc/g dry polymer;
wherein the Ratio of Pore Volume between 50 Å to 3,000 Å in diameter To Pore Volume between 500 Å to 3,000 Å in diameter of the said biocompatible polymer is smaller than 200:1; and
wherein the Ratio of Pore Volume between 50 Å to 3,000 Å in diameter To Pore Volume between 1,000 Å to 3,000 Å in diameter of said biocompatible polymer is greater than 20:1.

2. The method of claim 1, wherein said biocompatible polymer comprises particles having a diameter in the range for 0.1 microns to 2 centimeters.

3. The method of claim 1, wherein said biocompatible polymer is in the form of powder, beads or other regular or irregularly shaped particulate.

4. The method of claim 1, wherein said biocompatible polymer is a coated polymer comprising at least one crosslinking agent and at least one dispersing agent;
said dispersing agents selected from the group consisting of hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof;
said crosslinking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof;
said polymer being developed simultaneously with the formation of the coating, wherein said dispersing agent is chemically bound to said surface of said biocompatible polymer.

5. The method of claim 4, wherein said biocompatible polymer comprises residues from one or more monomers selected from divnylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

6. The method of claim 1, wherein said biocompatible polymer is an ion exchange polymer.

7. The method of claim 1, wherein said biocompatible polymer is a cellulosic polymer.

8. The method of claim 1, wherein said biocompatible polymer is a porous highly crosslinked styrene or divinylbenzene copolymer.

9. The method of claim 8, wherein said porous highly crosslinked styrene or divinylbenzene copolymer is a macroporous or mesoporous styrene-divinylbenzene-ethylstyrene copolymer subjected to a partial chloromethylation to a chlorine content of up to 7% molecular weight.

10. The method of claim 8, wherein said porous highly crosslinked styrene or divinylbenzene copolymer is a hypercrosslinked polystyrene produced from crosslinked styrene copolymers by an extensive chloromethylation and a subsequent post-crosslinking by treating with a Friedel-Crafts catalyst in a swollen state.

11. The method of claim 1, wherein said biocompatible polymer is a hydrophilic self-wetting polymer that can be administered as dry powder or dry particulate containing hydrophilic functional groups selected from the group consisting of chlorine, amines, hydroxyl, sulfonate, and carboxyl groups.

12. The method of claim 1, wherein said biocompatible polymer is pyrolyzed.

13. The method of claim 1, wherein the sorbent in contained within a cartridge.

14. The method of claim 1, wherein said contacting comprises:
removing blood from the patient;
contacting said blood with said sorbent external to said patient's body; and
returning said blood to said patient.

15. The method of claim 14, wherein said sorbent is contained within a cartridge and the removing and the returning are part of a continuous circuit connecting an appropriate artery within the patient and an appropriate vein within the patient.

* * * * *